United States Patent [19]

Buschmann et al.

[11] 4,328,380
[45] May 4, 1982

[54] SUBSTITUTED PHENYLPROPYL HALIDES

[75] Inventors: Ernst Buschmann, Ludwigshafen; Norbert Goetz, Worms; Bernd Zeeh, Ludwigshafen; Juergen Varwig, Heidelberg, all of Fed. Rep. of Germany

[73] Assignee: BASF Aktiengesellschaft, Fed. Rep. of Germany

[21] Appl. No.: 176,456

[22] Filed: Aug. 8, 1980

Related U.S. Application Data

[62] Division of Ser. No. 38,274, May 11, 1979, Pat. No. 4,250,123.

[30] Foreign Application Priority Data

Jul. 8, 1978 [DE] Fed. Rep. of Germany ....... 2830120

[51] Int. Cl.$^3$ ............................................. C07C 21/24
[52] U.S. Cl. ..................................... 570/191; 570/190
[58] Field of Search .......................................... 570/191

[56] References Cited

U.S. PATENT DOCUMENTS

| | | | |
|---|---|---|---|
| 2,349,779 | 5/1944 | Van Zoeren | 570/194 |
| 2,485,017 | 10/1949 | Schmerling | 570/194 |
| 3,904,667 | 9/1975 | Martin | 260/465 G |
| 3,962,307 | 6/1976 | Martin | 260/465 G |

FOREIGN PATENT DOCUMENTS 2656747 12/1976 Fed. Rep. of Germany .
2752135 11/1977 Fed. Rep. of Germany .

OTHER PUBLICATIONS

Volkor et al., Dokl. Akad. Nauk SSSR, 133, 843 (1960).
Monteils, Bull. Soc. Chim. France, p. 637 (1951).
Baddeley et al., J. Chem. Soc., p. 4647 (1956).
Ross et al., *Friedel Crafts and Related Reactions*, vol. II, p. 786, Interscience (1964).

*Primary Examiner*—Curtis R. Davis
*Attorney, Agent, or Firm*—Keil & Witherspoon

[57] ABSTRACT

A novel process for the preparation of phenylpropyl halides of the formula

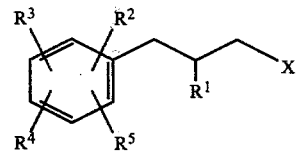

by reacting the corresponding phenylpropyl halides, substituted only by $R^2$ and $R^1$, with an alcohol, alkyl halide or olefin; and phenylpropyl halides where $R^3$ has certain meanings.

5 Claims, No Drawings

SUBSTITUTED PHENYLPROPYL HALIDES

This is a division, of application Ser. No. 38,274, filed May 11, 1979 now U.S. Pat. No. 4,250,123.

The present invention relates to a process for the preparation of substituted phenylpropyl halides by reacting phenylpropyl halides with alcohols, alkyl halides or olefins in the presence of acid catalysts, and to the products thus obtainable. These are important starting compounds for the preparation of correspondingly substituted morpholines or piperidines, which may be used for combating fungi.

The preparation of alkylaromatics from aromatics and olefins, using a strongly acid catalyst, eg. sulfuric acid or phosphoric acid, is known (Friedel-Crafts and Related Reactions, George A. Olah, volume II, pages 1–288, 1964). For example, p-tert.-butyltoluene is obtained in very good yield by alkylating toluene with isobutylene. If instead of toluene aromatics with longer alkyl chains (eg. ethylbenzene or propylbenzene) are employed, the reaction takes place distinctly more slowly (R. N. Volkor and S. V. Zavgorodnij, Dokl. Akad. Nauk S.S.S.R. 133, 843 (1960)). Only one example of the alkylation, under conventional conditions, of aromatics having a labile halogenated side chain has been disclosed (Y. Monteils, Bull. Soc. Chim. France, page 637 (1951), and this shows an unsatisfactory yield.

We have found that a phenylpropyl halide of the general formula

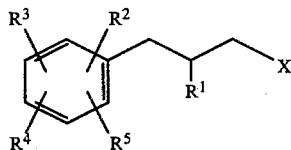

where $R^1$ is hydrogen or an aliphatic radical of 1 to 10 carbon atoms, $R^2$ is hydrogen, alkyl of 1 to 3 carbon atoms, fluorine or methoxy, $R^3$ is an aliphatic radical of 2 to 20 carbon atoms, a cycloaliphatic or bicycloaliphatic radical of 5 to 7 carbon atoms or haloalkyl of 3 to 10 carbon atoms, $R^4$ and $R^5$ independently of one another are each hydrogen, chlorine, bromine, nitro or acetyl and X is chlorine or bromine, is obtained in a simple manner and in good yields when a phenyl halide of the formula

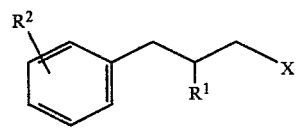

where $R^1$, $R^2$ and X have the above meanings, is reacted, in the presence of an acid catalyst, with an alcohol of the formula $R^3OH$ or an alkyl halide of the formula $R^3Hal$, where Hal is halogen, or with an olefin corresponding to the compound $R^3H$, where $R^3$ has the above meanings, and, where required, the reaction product obtained is converted to the corresponding halogen derivative, nitro derivative or acetyl derivative.

The substituted phenylpropyl halides obtainable by this process can for example be reacted with unsubstituted or substituted morpholines or piperidines to give compounds which possess a good fungicidal action and can be used as fungicides (cf. German Offenlegungsschriften DOS Nos. 2,656,747 and 2,752,135).

Substituted phenylpropyl halides which are particularly suitable for the preparation of fungicidal active ingredients, in accordance with the above reaction, are those of the general formula

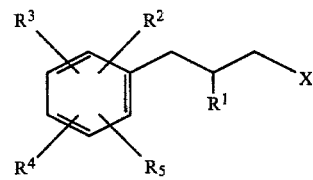

where $R^1$ is hydrogen or an aliphatic radical of 1 to 10 carbon atoms, $R^2$ is hydrogen, alkyl of 1 to 3 carbon atoms, fluorine or methoxy, $R^3$ is an aliphatic radical of 2 to 20 carbon atoms, a cycloaliphatic or bicycloaliphatic radical of 5 to 7 carbon atoms or haloalkyl of 3 to 10 carbon atoms, $R^4$ and $R^5$ are each independently of one another hydrogen, chlorine, bromine, nitro or acetyl, and X is chlorine or bromine, with the proviso that $R^3$ is haloalkyl of 3 to 10 carbon atoms if $R^2$, $R^4$ and $R^5$ are simultaneously hydrogen.

For example, reaction of 3-[p-(1-chloromethyl-1-methyl-ethyl)-phenyl]-2-methyl-propyl chloride with cis-2,6-dimethylmorpholine gives N-[3-(p-1-chloromethyl-1-methyl-ethyl-phenyl)-2-methyl]-propyl-2,6-cis-dimethyl-morpholine by the following method: a mixture of 24 g of 3-p-(1-chloromethyl-1-methyl-ethyl-phenyl)-2-methyl-propyl chloride and 32 g of cis-2,6-dimethylmorpholine is heated for 4 hours at 150° C. The crude product is dissolved in chloroform, the solution is repeatedly washed with water and dried over Na₂SO₄, the solvent is evaporated off and the residue is distilled. This gives 21 g of N-[3-(p-1-chloromethyl-1-methyl-ethyl-phenyl)-2-methyl]-propyl-2,6-cis-dimethyl-morpholine, boiling point 165° C.-166° C./0.1 mm Hg.

Examples of $R^1$ are hydrogen, methyl, ethyl, propyl, isopropyl, 1-methyl-propyl, 2-methyl-propyl, butyl, pentyl and hexyl. Examples of $R^2$ are hydrogen, fluorine, methyl, ethyl, propyl and methoxy.

Examples of $R^3$ are tert.-butyl, tert.-amyl, 1-ethyl-1-methyl-propyl, 1,1-diethyl-propyl, 1,1-dimethyl-butyl, 1,1-dimethyl-pentyl, cyclopentyl, cyclohexyl, cycloheptyl, norbornyl, 1-chloromethyl-1-methyl-ethyl and 3-chloro-1,1-dimethyl-propyl.

The starting compounds for the process are phenylpropyl halides of the formula

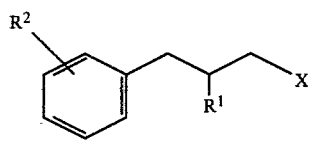

where $R^1$, $R^2$ and X have the above meanings, and these halides are obtainable by conventional reactions, in accordance with the scheme shown below

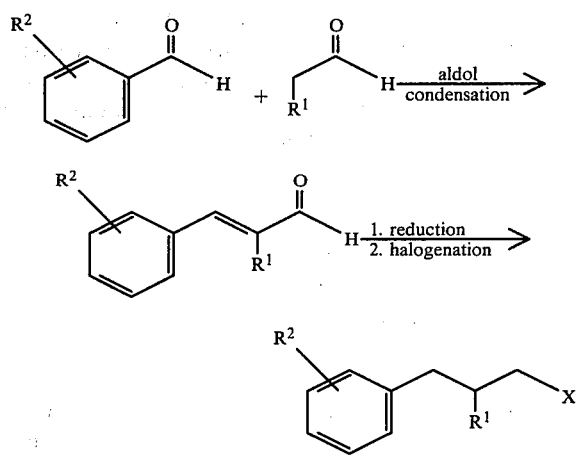

(cf. inter alia, G. Baddeley and R. Williamson, J. Chem. Soc. 1956, 4,651).

The other starting compounds are olefins corresponding to the compound $R^3H$, where $R^3$ has the above meanings. Examples of such olefins are ethylene, n-pent-1-ene, n-hex-1-ene, n-hept-1-ene, n-oct-1-ene, n-non-1-ene, n-dec-1-ene, n-undec-1-ene, n-dodec-1-ene, propyl-1-ene and n-but-1-ene; the above alkenes substituted by methyl, ethyl, n-propyl, isopropyl, n-butyl, isobutyl, sec.-butyl or tert.-butyl in the 2-, 3- or 4-position; 2,3-dimethyl-n-butene, 3,3-dimethyl-n-butene, 2,5-dimethylheptene, 3,3-dimethylheptene, 2,3,4-trimethylheptene, 2,4-dimethylheptene, 2,3-diethylheptene, 4,4-dimethylheptene, 2,3-diethylhexene, 4,4-dimethylhexene, 2,3-dimethylhexene, 2,4-dimethylhexene, 2,5-dimethylhexene, 3,3-dimethylhexene, 3,4-dimethylhexene, 2-methyl-3-ethylpentene, 3-methyl-3-ethylpentene, 2,3,3-trimethylheptene, 2,4,4-trimethylpentene, 2,3,3-trimethylpentene, 2,3,4-trimethylpentene and 2,3,3,4-tetramethylpentene; corresponding alkenes where the double bond is in the 2-position or 3-position of the molecule; branched alkenes, such as are obtained as mixtures on dimerizing isobutylene or n-butene (giving octenes) or trimerizing isobutylene or n-butene (giving dodecenes) or trimerizing propylene (giving nonenes) or tetramerizing propylene (giving dodecenes); the cyclic and bicyclic olefins, such as cycloheptene, cyclohexene, cyclopentene and norbornene, and the haloolefins, such as vinyl bromide, allyl chloride, allyl bromide, 1,3-dichloropropene, methylallyl chloride, crotyl chloride, 1,3-dichloro-2-methyl-prop-1-ene 2-methyl-allyl chloride, 2-chloro-methyl-allyl chloride and 4-chloro-2-methyl-but-1-ene.

Norbornene, cyclopentene, cyclohexene, cycloheptene, isobutylene, hept-1-ene and methallyl chloride are preferred.

Alternatively to the olefins, halides of the formula $R^3Hal$ may be used as starting materials, for example the following compounds: ethyl bromide, n-propyl chloride, n-propyl bromide, isopropyl chloride, isopropyl bromide, n-butyl chloride, s-butyl chloride, isobutyl chloride, t-butyl chloride, isoamyl chloride, t-amyl chloride, t-amyl bromide, neopentyl chloride, 1,1-diethylethyl chloride, 1,1-diethyl-propyl chloride, 1,1-dimethylbutyl chloride, 1,1-dimethylpentyl chloride, 1,3-dichloro-1,1-dimethylpropane, cyclopentyl chloride, 2-chloro-2-methylpentane, 3-chloro-3-methylpentane, cyclohexyl chloride, 3-chloro-2-methylhexane, 3-chloro-3-ethylpentane, 2,4-dimethyl-2-chloropentane, 3-methylcyclohexyl chloride, 4-chloro-4-methylheptane, 2-chloro-2,5-dimethylhexane, 3-chloro-3-ethylhexane, 4-chloro-4-ethylheptane, 3-chloro-3,6-dimethylheptane, 3-chloro-3-ethyl-5-methylhexane, 4-chloro-4n-propylheptane, 4-chloro-2,4,6-trimethylheptane, methyl chloride, 4-chloro-4n-propyl-2-methylheptane, 5-phenyl-1-chloropentane, 5-chloro-2,5,8-trimethylnonane, 5-chloro-2,8-dimethyl-5-ethylnonane, 5-chloro-2,8-dimethyl-5n-propylnonane, 5chloro-2,8-dimethyl-5-isobutylnonane, n-octadecyl bromide, 1,3-dichloro-1,1-dimethylpropane and 1,2,3-trichloro-1,1-dimethylpropane. Preferred halides are tert.-butyl chloride, tert.-amyl chloride, 1,1-diethyl-ethyl chloride, 1,1-diethyl-propyl chloride, 1,1-dimethylbutyl chloride, 1,1-dimethyl-pentyl chloride and 1,3-dichloro-1,1-dimethylpropane.

As yet a further alternative, alcohols of the formula $R^3OH$ may be used, for example the following: methanol, ethanol, n-propanol, isopropanol, n-butanol, s-butanol, isobutanol, t-butanol, n-amyl alcohol, 2-pentanol, 3-methyl-2-butanol, t-amyl alcohol, neopentyl alcohol, cyclobutylcarbinol, 2-methyl-2-pentanol, 2,3-dimethyl-2-butanol, cyclohexanol, cyclopentylcarbinol, cyclohexylcarbinol, n-octyl alcohol, 2-methyl-2-heptanol, 2,3-dimethyl-2-hexanol, 2,4-dimethyl-2-hexanol, 3-ethyl-2methyl-2-pentanol, 2,3,3-trimethyl-2-pentanol, 2,4,4-trimethyl-2-pentanol, α-phenylpropanol and α-dodecyl alcohol. Tert.-butanol and t-amyl alcohol are preferred.

Examples of acid catalysts which can be used are $AlCl_3$, $AlBr_3$, $FeCl_3$, $TiCl_4$, $ZrCl_4$, $VCl_4$, $ZnCl_2$, $ZnCl_2 \cdot Al_2O_3$, $ZnCl_2 \cdot SiO_2$, $BF_3$, $BF_3 \cdot 2H_2O$, $BF_3 \cdot H_2SO_4$, $BF_3 \cdot H_3PO_4$, $HBr$, $H_2SO_4$, $H_3PO_4$, $HF$, $FSO_3H$, $HF$, $FSO_3H$, $P_2O_5$, polyphosphoric acid, $SiO_2 \cdot Al_2O_3$, $CH_3SO_3H$ and its homologs, $ClSO_3H$, $HClO_4$, toluenesulfonic acid and organic cation exchangers containing sulfonic acid groups.

$HF$, $H_2SO_4$, $FeCl_3$ and $BF_3 \cdot 2H_2O$ are preferred.

In the reaction, the acid catalyst is present, for example, in an amount of from 5 to 100 percent by weight, based on the phenylpropyl halide starting material.

The reaction is carried out at, for example, from $-10°$ C. to 250° C., preferably at 5° C.–50° C., under atmospheric or superatmospheric pressure. It takes place in accordance with the following equation:

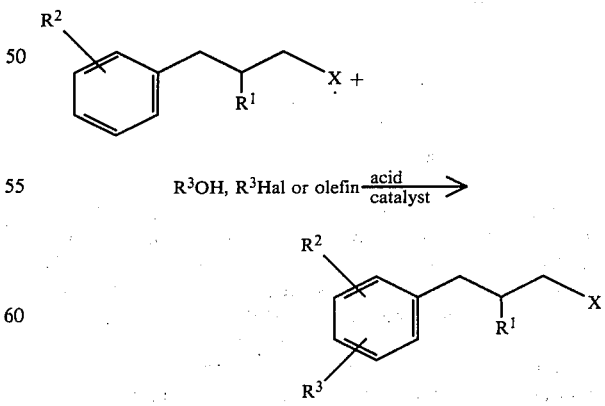

The reaction can, for example, be carried out as follows: The alkylating agent is added to the mixture of catalyst and halide, with or without a solvent. At the end of the reaction the catalyst is separated off and, if necessary, the crude product is taken up in an organic solvent, and the solution is washed with water and distilled.

Examples of suitable organic solvents are CHCl₃, dichloroethane, light naphtha, cyclohexane, CH₂Cl₂, CS₂, nitrobenzene, chlorobenzene and dichlorobenzene.

The alkyl-substituted phenylpropyl halides thus obtained can, if desired, be converted in subsequent reaction steps to the corresponding halogen nitro or acetyl derivatives, in accordance with the scheme shown below, where R¹, R², R³, R⁴, R⁵ and X have the above meanings:

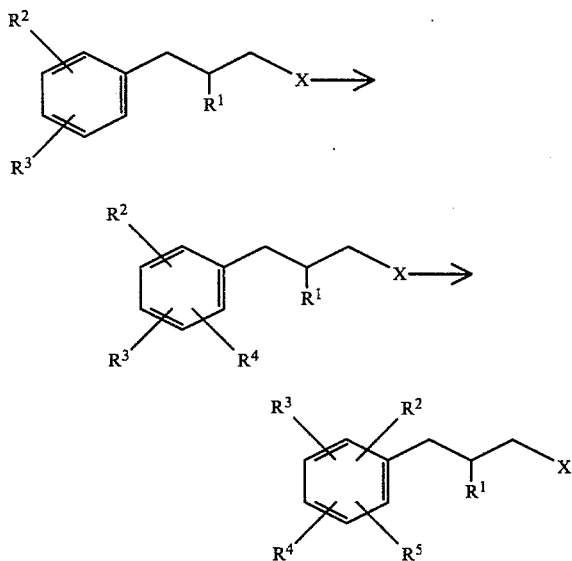

The halogenation is, for example, carried out conventionally by reaction with a halogen and iron powder. The nitration is, for example, carried out conventionally by reaction with a mixture of sulfuric acid and nitric acid. The acetylation is carried out, for example, as described by G. Baddelay, J. Chem. Soc. 1956, 4,647.

The Examples which follow illustrate how the process may be carried out.

EXAMPLE I

Preparation of 3-(4-tert.-butylphenyl)-propyl chloride 23 parts by weight of isobutylene are passed into a mixture of 62 parts by weight of 3-phenylpropyl chloride and 13 parts by weight of 96% strength by weight sulfuric acid at 10° C. Stirring is continued for 3 hours at room temperature (20° C.). The crude product is dissolved in CHCl₃, and the solution is thoroughly washed with ice water, dried over Na₂CO₃ and distilled.

57 parts by weight of 3-(4-tert.-butylphenyl)-propyl chloride, boiling point 108° C.-110° C./0.2 mm Hg, are obtained.

Yield 65% (based on 3-phenylpropyl chloride).

EXAMPLE II

Preparation of 3-(4-cyclopentylphenyl)-propyl bromide 10 parts by weight of cyclopentene are added dropwise, at 10° C., to a mixture of 30 parts by weight of p-phenylpropyl bromide and 20 parts by weight of 96% strength sulfuric acid. Stirring is continued for 14 hours at room temperature (20° C.). The crude product is dissolved in CHCl₃ and the solution is thoroughly washed with ice water, dried over Na₂CO₃ and distilled. 25 parts by weight of 3-(4-cyclopentylphenyl)-propyl bromide are obtained. Boiling point 160° C.-163° C./0.5 mm Hg, yield 60% (based on 3-phenylpropyl bromide).

EXAMPLE III

Preparation of 3-(4-cyclohexylphenyl)-propyl bromide 17 parts by weight of cyclohexene are added dropwise at +10° C. to a mixture of 40 parts by weight of 3-phenylpropyl bromide and 20 parts by weight of 96% strength sulfuric acid. Stirring is continued for 14 hours at room temperature. The crude product is dissolved in CHCl₃ and the solution is thoroughly washed with ice water, dried over Na₂CO₃ and distilled. 35 parts by weight of 3-(4-cyclohexylphenyl)-propyl bromide are obtained.

EXAMPLE IV

Preparation of 3-(4-cyclohexylphenyl)-propyl chloride 16.5 parts by weight of cyclohexene are added dropwise at +10° C. to a mixture of 31 parts by weight of 3-phenylpropyl chloride and 20 parts by weight of 96% strength sulfuric acid. Stirring is continued for 14 hours at room temperature. The crude product is dissolved in CHCl₃/ice water and the organic solution is thoroughly washed with ice water, dried over Na₂CO₃ and distilled. 27 parts by weight of 3-(4-cyclohexylphenyl)-propyl chloride are obtained; boiling point 126° C.-130° C./0.2 mm Hg, yield 57%(based on 3-phenylpropyl chloride).

EXAMPLE V

Preparation of 3-(4-norbornylphenyl)-propyl chloride 28 parts by weight of fused norbornene are added dropwise at 10° C. to a mixture of 46 parts by weight of 3-phenylpropyl chloride and 30 parts by weight of 96% strength sulfuric acid. Stirring is continued for 14 hours at room temperature. The crude product is dissolved in CHCl₃ and the solution is thoroughly washed with ice water, dried over Na₂CO₃ and distilled. 61 parts by weight of 3-(4-norbornylphenyl)-propyl chloride are obtained; boiling point 160° C.-164° C./0.1 mm Hg, yield 81% (based on 3-phenylpropyl chloride).

EXAMPLE VI

Preparation of 2-methyl-3-(4-norbornylphenyl)-propyl chloride 24 parts by weight of fused norbornene are added dropwise at 10° C. to a mixture of 42 parts by weight of 2-methyl-3-phenyl-propyl chloride and 22 parts by weight of 96% strength sulfuric acid. Stirring is continued for 14 hours at room temperature. The crude product is dissolved in CHCl₃, and the solution is thoroughly washed with ice water, dried over Na₂CO₃ and distilled. 50 parts by weight of 2-methyl-3-(4-norbornylphenyl)-propyl chloride areobtained; boiling point 128° C.-130° C./0.1 mm Hg, yield 76% (based on 2-methyl-3-phenylpropyl chloride).

EXAMPLE VII

Preparation of 3-(4-cyclohexylphenyl)-2-methylpropyl chloride 33 parts by weight of cyclohexene are added dropwise to a mixture of 67 parts by weight of 2-methyl-3-phenylpropyl chloride and 40 parts by weight of 96% strength sulfuric acid at 10° C. Stirring is continued for 14 hours at room temperature. The crude product is dissolved in $CHCl_3$ and the solution is thoroughly washed with ice water, dried over $Na_2CO_3$ and distilled. 70 parts by weight of 3-(4-cyclohexylphenyl)-2-methyl-propyl chloride are obtained; boiling point 130° C.-2° C./0.1 mm Hg, yield 70% (based on 2-methyl-3-phenylpropyl chloride).

EXAMPLE VIII

Preparation of 3-(4-heptylphenyl)-2-methylpropyl chloride 25 parts by weight of hept-1-ene are added dropwise at 10° C. to a mixture of 42 parts by weight of 2-methyl-3-phenylpropyl chloride and 20 parts by weight of 96% strength sulfuric acid. Stirring is continued at room temperature for 14 hours. The crude product is dissolved in $CHCl_3$, and the solution is washed with ice water, dried over $Na_2CO_3$ and distilled. 50 parts by weight of 3-(4-heptylphenyl)-2-methyl-propyl chloride are obtained; boiling point 114° C.-7° C./0.1 mm Hg, yield 75% (based on 2-methyl-3-phenylpropyl chloride).

EXAMPLE IX

Preparation of 3-p-(1-chloromethyl-1-methyl-ethyl)-phenyl-2-methyl-propyl chloride 9 parts by weight of 2-methallyl chloride are added dropwise at 10° C. to a mixture of 17 parts by weight of 2-methyl-3-phenyl-propyl chloride and 10 parts by weight of 96% strength sulfuric acid. Stirring is continued at room temperature for 14 hours, the crude product is dissolved in $CHCl_3$ and the solution is washed with water, dried over $Na_2CO_3$ and distilled. 14 parts by weight of 3-p-(1-chloromethyl-1-methyl-ethyl)-phenyl-2-methyl-propyl chloride are obtained; boiling point 129° C.-131° C./0.1 mm Hg, yield 54% (based on 2-methyl-3-phenyl-propyl chloride).

EXAMPLE X

Preparation of 2-methyl-3-(p-tert.-butylphenyl)-propyl chloride by alkylating 2-methyl-3-phenyl-propyl chloride by various methods (A) Concentrated sulfuric acid and isobutylene.

31 parts by weight of isobutylene are passed into a mixture of 84 parts by weight of 2-methyl-3-phenylpropyl chloride and 12.8 parts by weight of 96% strength sulfuric acid at +10° C. Stirring is then continued for 3 hours at 10° C. The mixture is then allowed to warm to room temperature (20° C.), the sulfuric acid phase is separated off and the organic phase is washed with 100 parts by volume of 20% strength sodium hydroxide solution. For better phase separation, 50 parts by volume of acetone are added. The organic phase is then separated off and distilled.

16 parts by weight of 2-methyl-3-phenyl-propyl chloride, boiling point 105° C./16 mm Hg and 75 parts by weight of 2-methyl-3-(p-tert.-butylphenyl)-propyl chloride, boiling point 80° C.-81° C./0.02 mm Hg, are obtained.

The conversion is 81% and the yield is 82.5% of theory (based on 2-methyl-3-phenyl-propyl chloride converted).

(B) Anhydrous $FeCl_3$ and isobutylene 20.3 parts by weight of finely divided anhydrous iron-(III) chloride are added to 84 parts by weight of 2-methyl-3-phenylpropyl chloride at 10° C. 31 parts by weight of isobutylene are then passed into this mixture at 10° C. and after completion of the introduction stirring is continued for 3 hours at 10° C. The mixture is then allowed to warm to room temperature, 100 parts by volume of water are added whilst stirring and cooling, and the solid material is filtered off.

The filtrate consists of an aqueous and an organic phase. The latter is separated off and distilled.

5 parts by weight of 2-methyl-3-phenyl-propyl chloride, boiling point 105° C./16 mm Hg, and 74.5 parts by weight of 2-methyl-3-(p-tert.-butylphenyl)-propyl chloride, boiling point 80° C.-81° C./0.02 mm Hg, are obtained.

The conversion is 94% and the yield is 70% of theory (based on 2-methyl-3-phenyl-propyl chloride converted).

(C) Boron trifluoride and tert.-butyl chloride.

$BF_3$ is passed for 30 minutes into a mixture of 84 parts by weight of 2-methyl-3-phenyl-propyl chloride and 50 ml of $BF_3 \cdot 2H_2O$ at room temperature. 56 parts by weight of tert.-butyl chloride are then added dropwise at room temperature. The mixture is refluxed for 4 hours and is then allowed to cool; the crude product is introduced into water and extracted with chloroform. The organic phase is separated off, washed with water, dried over $Na_2CO_3$ and distilled. 30 parts by weight of 2-methyl-3-phenyl-propyl chloride, boiling point 105° C./16 mm Hg, and 45 parts by weight of 2-methyl-3-(p-tert.-butylphenyl)-propyl chloride, boiling point 80° C.-81° C./0.02 mm Hg, are obtained.

The conversion is 64% and the yield is 63% based on 2-methyl-3-phenylpropyl chloride converted.

(D) Hydrogen fluoride and isobutene.

20 parts by weight of isobutene are passed into a mixture of 68 parts by weight of 2-methyl-3-phenylpropyl chloride and 3 parts by weight of hydrogen fluoride at 0° C. The mixture is then stirred for 12 hours at room temperature. The crude product is washed with water, dried over $Na_2CO_3$ and distilled. 36 parts by weight of 2-methyl-3-phenylpropyl chloride, boiling point 105° C./16 mm Hg and 32 parts by weight of 2-methyl-3-(p-tert.-butylphenyl)-propyl chloride, boiling point 80° C.-81° C./0.02 mm Hg, are obtained.

The conversion is 47% and the yield is 75%, based on 2-methyl-3-phenylpropyl chloride converted.

(E) Iron-(III) chloride and tert.-butyl chloride.

61 parts by weight of tert.-butyl chloride are added dropwise at 30° C. to a mixture of 100 parts by weight of 2-methyl-3-phenyl-propyl chloride and 8.1 parts by weight of anhydrous finely divided iron(III) chloride. The mixture is then stirred for 14 hours at room temperature. The crude product is poured into ice water and repeatedly extracted with $CHCl_3$, and the chloroform solution is separated off, dried with $Na_2CO_3$ and distilled.

42 parts by weight of 2-methyl-3-phenyl-propyl chloride, boiling point 105° C./16 mm Hg, and 55 parts by weight of 2-methyl-3-(p-tert.-butylphenyl)-propyl chloride, boiling point 80° C.–82° C./0.02 mm Hg, are obtained.

The conversion is 58% and the yield is 71%, based on 2-methyl-3-phenyl-propyl chloride converted.

EXAMPLE XI

Preparation of 3-(5-tert.-butyl-2-methoxy-phenyl)-2-methyl-propyl chloride 122 parts by weight of tert.-butyl chloride are added dropwise, at 30° C., to a mixture of 234 parts by weight of 3-(2-methoxy-phenyl)-2-methyl-propyl chloride and 19.4 parts by weight of anhydrous iron-(III) chloride. The mixture is stirred for 8 hours at 50° C. and 14 hours at room temperature. The crude product is poured into ice water and dissolved in CHCl$_3$, the solution is repeatedly washed with water and dried over Na$_2$CO$_3$, the solvent is evaporated and the residue is distilled.

110 parts by weight of 3-(5-tert.-butyl-2-methoxy-phenyl)-2-methyl-propyl chloride, boiling point 105° C.–108° C./0.1 mm Hg, are obtained.

EXAMPLE XII

Preparation of 3-(5-tert.-butyl-2-methyl-phenyl)-2-methyl-propyl chloride and 3-(4-tert.-butyl-2-methyl-phenyl)-2-methyl-propyl chloride 62 parts by weight of isobutylene are passed into a mixture of 200 parts by weight of 3-(2-methyl-phenyl)-2-methyl-propyl chloride and 98 parts by weight of 96% strength sulfuric acid at +10° C. The mixture is then stirred for 3 hours at 10° C., after which it is allowed to warm to room temperature, the sulfuric acid phase is separated off and the organic phase is washed with 100 parts by volume of 20% strength sodium hydroxide solution. For better phase separation, 50 parts by volume of acetone are added. The organic phase is then separated off and distilled.

A mixture consisting of 3-(5-tert.-butyl-2-methyl-phenyl)-2-methyl-propyl chloride and 3-(4-tert.-butyl-2-methyl-phenyl)-2-methyl-propyl chloride is obtained. Boiling point 106° C./0.1 mm Hg.

EXAMPLE XIII

Preparation of 3[p-(1-methyl-1-ethyl-propyl)-phenyl]-2-methyl-propyl chloride 365 parts by weight of 1-methyl-1-ethyl-propyl chloride are added dropwise to a mixture of 510 parts by weight of 2-methyl-3-phenyl-propyl chloride and 49 parts by weight of anhydrous iron (III) chloride at 30° C. The resulting mixture is stirred for 8 hours at 50° C. and for 14 hours at room temperature (20° C.). The crude product is poured into ice water and dissolved in CHCl$_3$, the solution is repeatedly washed with water and dried over Na$_2$CO$_3$, the solvent is evaporated and the residue is distilled.

420 parts by weight of 3-[p-(1-methyl-1-ethyl-propyl)-phenyl]-2-methyl-propyl chloride are obtained. Boiling point 125° C./0.1 mm Hg.

EXAMPLE XIV

Preparation of 3-(p-tert.-butyl-o-bromo-phenyl)-2-methyl-propyl chloride 16 parts by weight of bromine are added dropwise to a mixture of 23 parts by weight of 3-(p-tert.-butyl-phenyl)-2-methyl-propyl chloride and 0.5 part by weight of iron powder. The reaction temperature rises to 35° C. Stirring is continued for 17 hours, the product is dissolved in chloroform, the solution is washed with water, with aqueous NaHCO$_3$ solution and again with water and is dried over Na$_2$SO$_4$, the solvent is evaporated and the residue is distilled.

20 parts by weight of 3-(p-tert.-butyl-o-bromo-phenyl)-2-methyl-propyl chloride are obtained. Boiling point 111° C.–115° C./0.1 mm Hg.

EXAMPLE XV

Preparation of 3-(p-tert.-butyl-o-chlorophenyl)-2-methyl-propyl chloride and 3-(p-tert.-butyl-m-chloro-phenyl)-2-methyl-propyl chloride 101 parts by weight of chlorine gas are passed into a mixture of 320 parts by weight of 3-(p-tert.-butyl-phenyl)-2-methyl-propyl chloride and 2 parts by weight of iron powder at 30° C.–35° C. The mixture is stirred for a further hour and the crude product is poured into ice water. The organic phase is washed with water, with aqueous NaHCO$_3$ solution and again with water and is dried over Na$_2$SO$_4$, the solvent is evaporated and the residue is distilled. 300 parts by weight of a mixture of 3-(p-tert.-butyl-o-chloro-phenyl)-2-methyl-propyl chloride and 3-(p-tert.-butyl-m-chloro-phenyl)-2-methyl-propyl chloride are obtained. Boiling point 106° C.–111° C./0.1 mm Hg.

EXAMPLE XVI

Preparation of 3-(p-tert.-amyl-o-chloro-phenyl)-2-methyl-propyl chloride and 3-(p-tert.-amyl-m-chloro-phenyl)-2-methyl-propyl chloride 63 parts by weight of chlorine gas are passed into a mixture of 177 parts by weight of 3-(p-tert.-amyl-phenyl)-2-methyl-propyl chloride and 1 part by weight of iron powder at 30° C.–35° C. The mixture is then stirred for 14 hours at room temperature, after which it is dissolved in chloroform, the solution is washed with water, with 10% strength sodium hydroxide solution and again with water and is dried over Na$_2$SO$_4$, the solvent is evaporated and the residue is distilled.

110 parts by weight of a mixture of 3-(p-tert.-amyl-o-chlorophenyl)-2-methyl-propyl chloride and 3-(p-tert.-amyl-m-chloro-phenyl)-2-methyl-propyl chloride are obtained.
Boiling point 118° C.–120° C./0.1 mm Hg.

EXAMPLE XVII

Preparation of 3-(p-tert.-butyl-o-nitro-phenyl)-2-methyl-propyl chloride 440 parts by weight of nitrating acid, consisting of 200 parts by weight of concentrated nitric acid and 240 parts by weight of concentrated sulfuric acid, are added dropwise to 448 parts by weight of 3-(p-tert.-butyl-phenyl)-2-methyl-propyl chloride, whilst cooling with ice. After stirring has been continued for 3 hours at room temperature, the crude product is poured onto ice and extracted with diethyl ether, the extract is washed with water, with aqueous NaHCO₃ solution and again with water and is dried over Na₂SO₄, the solvent is evaporated and the residue is distilled.

413 parts by weight of 3-(p-tert.-butyl-o-nitro-phenyl)-2-methyl-propyl chloride are obtained.

Boiling point 138° C.–140° C./0.1 mm Hg.

EXAMPLE XVIII

Preparation of 2-methyl-3-(o-acetyl-p-tert.-butyl-phenyl)-propyl chloride

A solution of 63 g of acetyl chloride and 53 g of aluminum chloride in 300 ml of methylene chloride is added dropwise to a solution of 60 g of 3-(p-tert.-butyl-phenyl)-2-methyl-propyl chloride in 50 ml of methylene chloride at 20° C. After stirring has been continued for 10 minutes at room temperature, the mixture is poured into ice water and extracted with methylene chloride, the extract is repeatedly washed with water and dried over Na₂SO₄, the solvent is evaporated and the residue is distilled.

30 g of 2-methyl-3-(o-acetyl-p-tert.-butyl-phenyl)-propyl chloride are obtained.

Boiling point 134° C./0.1 mm Hg.

EXAMPLE XIX

Preparation of 3-(p-tert.-butyl-o-chloro-phenyl)-2-methyl-propyl bromide (1) and 3-(p-tert.-butyl-m-chloro-phenyl)-2-methyl-propyl bromide (2)

This preparation is carried out similarly to Example XV.

Boiling point 120° C.–3° C./0.2 mm Hg; the product contains 70% of (1) and 30% of (2).

EXAMPLE XX

3-[p-(1,1-Dimethyl-butyl)-phenyl]-2-methyl-propyl chloride

The compound is prepared similarly to Example XE. Boiling point 116° C.–118° C./0.1 mm Hg.

EXAMPLE XXI

3-[p-(1-Ethyl-1-methyl-propyl)-o-chloro-phenyl]-2-methyl-propyl chloride and
3-[p-(1-ethyl-1-methly-propyl)-m-chloro-phenyl]-2-methyl-propyl chloride The compound is prepared similarly to Example XE. Boiling point 135° C.–138° C./0.1 mm Hg.

EXAMPLE XXII 3-(p-Methoxy-o-tert.-amyl-phenyl)-2-methyl-propyl chloride and
3-(p-methoxy-m-tert.-amyl-phenyl)-2-methyl-propyl chloride.

The compound is prepared similarly to Example XE. Boiling point 123° C.–125° C./0.1 mm Hg.

EXAMPLE XXIII 2-(p-tert.-Amyl-phenyl)-propyl chloride

The compound is prepared similarly to Example XE. Boiling point 114° C.–115° C./0.1 mm Hg.

We claim:

1. A process for the preparation of a phenylpropyl halide of the formula

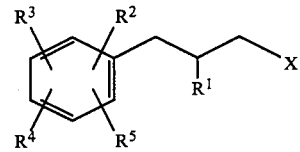

where $R^1$ is hydrogen or an aliphatic radical of 1 to 10 carbon atoms, $R^2$ is hydrogen, alkyl of 1 to 3 carbon atoms, fluorine or methoxy, $R^3$ is an aliphatic radical of 2 to 20 carbon atoms, a cycloaliphatic or bicycloaliphatic radical of 5 to 7 carbon atoms or haloalkyl of 3 to 10 carbon atoms, $R^4$ and $R^5$ independently of one another are each hydrogen, chlorine, bromine, nitro or acetyl and X is chlorine or bromine, wherein a phenylpropyl halide of the formula

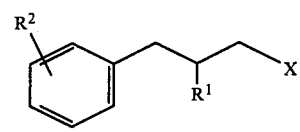

where $R^1$, $R^2$ and X have the above meanings, is reacted, in the presence of an acid catalyst, with an alcohol of the formula $R^3OH$ or an alkyl halide of the formula $R^3Hal$, where Hal is halogen, or with an olefin corresponding to the compound $R^3H$, where $R^3$ has the above meanings, and, where $R^4$ and $R^5$ are not both hydrogen, the reaction product obtained is further reacted to form the corresponding halogen derivative, nitro derivative or acetyl derivative.

2. The process of claim 1, wherein the 2-methyl-3-(p-tert.-butylphenyl)-propyl chloride is prepared by reacting 2-methyl-3-phenyl-propyl chloride with isobutylene.

3. The process of claim 2, wherein the acid catalyst is concentrated sulfuric acid, anhydrous FeCl₃ or hydrogen fluoride.

4. The process of claim 1, wherein the 2-methyl-3-(p-tert.-butylphenyl)-propyl chloride is prepared by reacting 2-methyl-3-phenyl-propyl chloride with tert.-butyl chloride.

5. The process of claim 4, wherein the acid catalyst is boron trifluoride or iron-(III) chloride.

* * * * *